(12) United States Patent
Bryant et al.

(10) Patent No.: US 6,749,573 B2
(45) Date of Patent: Jun. 15, 2004

(54) PASSIVE FETAL HEART MONITORING SYSTEM

(75) Inventors: Timothy D. Bryant, Gloucester, VA (US); Mark W. Wynkoop, Gloucester, VA (US); Nancy M. H. Holloway, Hayes, VA (US); Allan J. Zuckerwar, Williamsburg, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/784,414

(22) Filed: Feb. 13, 2001

(65) Prior Publication Data

US 2001/0034490 A1 Oct. 25, 2001

Related U.S. Application Data

(60) Provisional application No. 60/182,344, filed on Feb. 14, 2000.

(51) Int. Cl.[7] .............................................. A61B 7/00
(52) U.S. Cl. ...................................................... 600/528
(58) Field of Search ............................... 600/372, 376, 600/382, 386, 388, 390, 393, 508, 511, 514, 528, 586, 322, 131–136

(56) References Cited

U.S. PATENT DOCUMENTS

| | | | | |
|---|---|---|---|---|
| 4,212,368 A | * | 7/1980 | Allen | 181/131 |
| 4,398,116 A | | 8/1983 | Lewis | |
| 4,709,702 A | * | 12/1987 | Sherwin | 128/644 |
| 4,781,200 A | | 11/1988 | Baker | |
| 4,784,154 A | * | 11/1988 | Shirley et al. | 600/528 |
| 4,920,966 A | | 5/1990 | Hon et al. | |
| 4,928,786 A | * | 5/1990 | Allen | 181/137 |
| 5,140,992 A | * | 8/1992 | Zuckerwar et al. | 128/715 |
| 5,209,237 A | | 5/1993 | Rosenthal | |
| 5,467,775 A | * | 11/1995 | Callahan et al. | 600/528 |
| 5,492,129 A | | 2/1996 | Greenberger | |
| 5,885,222 A | | 3/1999 | Kassal et al. | |
| 6,245,025 B1 | | 6/2001 | Torok et al. | |

FOREIGN PATENT DOCUMENTS

| | | | |
|---|---|---|---|
| DE | 41 18359 A1 | 12/1992 | |
| EP | 0 310 380 A2 | 4/1989 | |
| EP | 0454931 | * 6/1991 | ............ A61B/7/04 |
| GB | 1 348 154 | 3/1974 | |
| WO | WO 95/06525 | 3/1995 | |
| WO | WO 98/37807 | 9/1998 | |

OTHER PUBLICATIONS

HTTP://Link.ABPI.Net/L.PHP?20031007A3, "Disposable Acoustic Pad Sensors," yet1.com.

* cited by examiner

*Primary Examiner*—Kennedy Schaetzle
*Assistant Examiner*—Kristen Droesch
(74) *Attorney, Agent, or Firm*—Helen M. Galus

(57) ABSTRACT

A fetal heart monitoring system preferably comprising a backing plate having a generally concave front surface and a generally convex back surface, and at least one sensor element attached to the concave front surface for acquiring acoustic fetal heart signals produced by a fetus within a body. The sensor element has a shape that conforms to the generally concave back surface of the backing plate. In one embodiment, the at least one sensor element comprises an inner sensor, and a plurality of outer sensors surrounding the inner sensor. The fetal heart monitoring system can further comprise a web belt, and a web belt guide movably attached to the web belt. The web belt guide being is to the convex back surface of the backing plate.

23 Claims, 20 Drawing Sheets

PASSIVE FETAL HEART MONITORING SYSTEM

CLAIM OF BENEFIT OF PROVISIONAL APPLICATION

Pursuant to 35 U.S.C. §119, the benefit of priority from provisional application 60/182,344, with a filing date of Feb. 14, 2000, is claimed for this non-provisional application.

ORIGIN OF THE INVENTION

The invention described herein was made by an employee of the United States Government and may be used by or for the Government for governmental purposes without the payment of any royalties thereon or therefor.

BACKGROUND OF THE INVENTION

1. Technical Field of the Invention

The present invention relates broadly to the field of biomedical transducers and more particularly, to a passive sensor monitoring the heart of a fetus.

2. Related Art and Problem to be Solved

Conventional fetal heart monitoring sensors are described in U.S. Pat. Nos. 4,471,200, 4,784,154, 5,209,237 and 5,524,631. Several known fetal heart sensors utilize a belt having one or more sensor stations thereon. Common shielding is used for all the sensor stations. However, in many instances, the common shielding crackles and moves thereby causing noise and interference of the detected fetal heart acoustic signal.

Some prior known heart monitoring sensors utilize a layer of RTV silicone to function as external pads that provide electrical isolation of the patient with respect to the belt sensor assembly. However, the RTV silicone layer is susceptible to chipping thereby reducing the electrical isolation between the belt sensor assembly and the patient.

Accordingly, it is an object of the present invention to provide a fetal heart monitoring sensor that substantially eliminates the problems associated with known fetal heart monitoring sensors.

Other objects and advantages of the present invention will in part be obvious and will in part be apparent from the specification.

SUMMARY OF THE INVENTION

The above and other objects and advantages, which will be apparent to one of skill in the art, are achieved in the present invention which, in one aspect, is directed to a fetal heart monitoring system comprising a backing plate which can have a generally concave front surface and a generally convex back surface, and at least one sensor element attached to the concave front surface for acquiring acoustic fetal heart signals produced by a fetus within a body. The sensor element can have a shape that conforms to the generally concave back surface of the backing plate. In one embodiment, the at least one sensor element comprises an inner sensor, and a plurality of outer sensors surrounding the inner sensor. In one embodiment, the fetal heart monitoring system further comprises a web belt, and a web belt guide movably attached to the web belt.

The web belt guide is attached to the convex back surface of the backing plate. In another aspect, the present invention is directed to a method for simultaneously making a plurality of acoustic signal sensor elements, comprising the steps of providing a plurality of flex cables wherein each flex cable has a plurality of conductors thereon, equidistantly positioning the flex cables along a working surface, configuring each flex cable such that all but a first one of the conductors are folded upward, disposing a first electrically conductive adhesive layer over a portion of the first one of the conductors of each flex cable, disposing a first strip of piezoelectric film over the first electrically conductive adhesive layer, configuring each flex cable such that a second one of the conductors is disposed over the first strip of piezoelectric film, disposing a second electrically conductive adhesive layer over a portion of the second one of the conductors of each flex cable, disposing a second strip of piezoelectric film over the second electrically conductive adhesive layer, configuring each flex cable such that a portion of a third one of the conductors of each flex cable is disposed over the second strip of piezoelectric film, disposing a third electrically conductive adhesive layer over said portion of the third one of the conductors, disposing a metallic strip over the third electrically conductive adhesive layer and substantially the entire second strip of piezoelectric film, curing the adhesive layers to form a laminate assembly, providing a template having indicia thereon that functions as a cutting guide, and cutting the laminate assembly according to the indicia to form a plurality of sensor elements.

BRIEF DESCRIPTION OF THE DRAWINGS

The features of the invention are believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DETAILED DESCRIPTION OF THE INVENTION

In describing the preferred embodiments of the present invention, reference will be made herein to FIGS. 1–20 of the drawings in which like numerals refer to like features of the invention.

Figure 1:
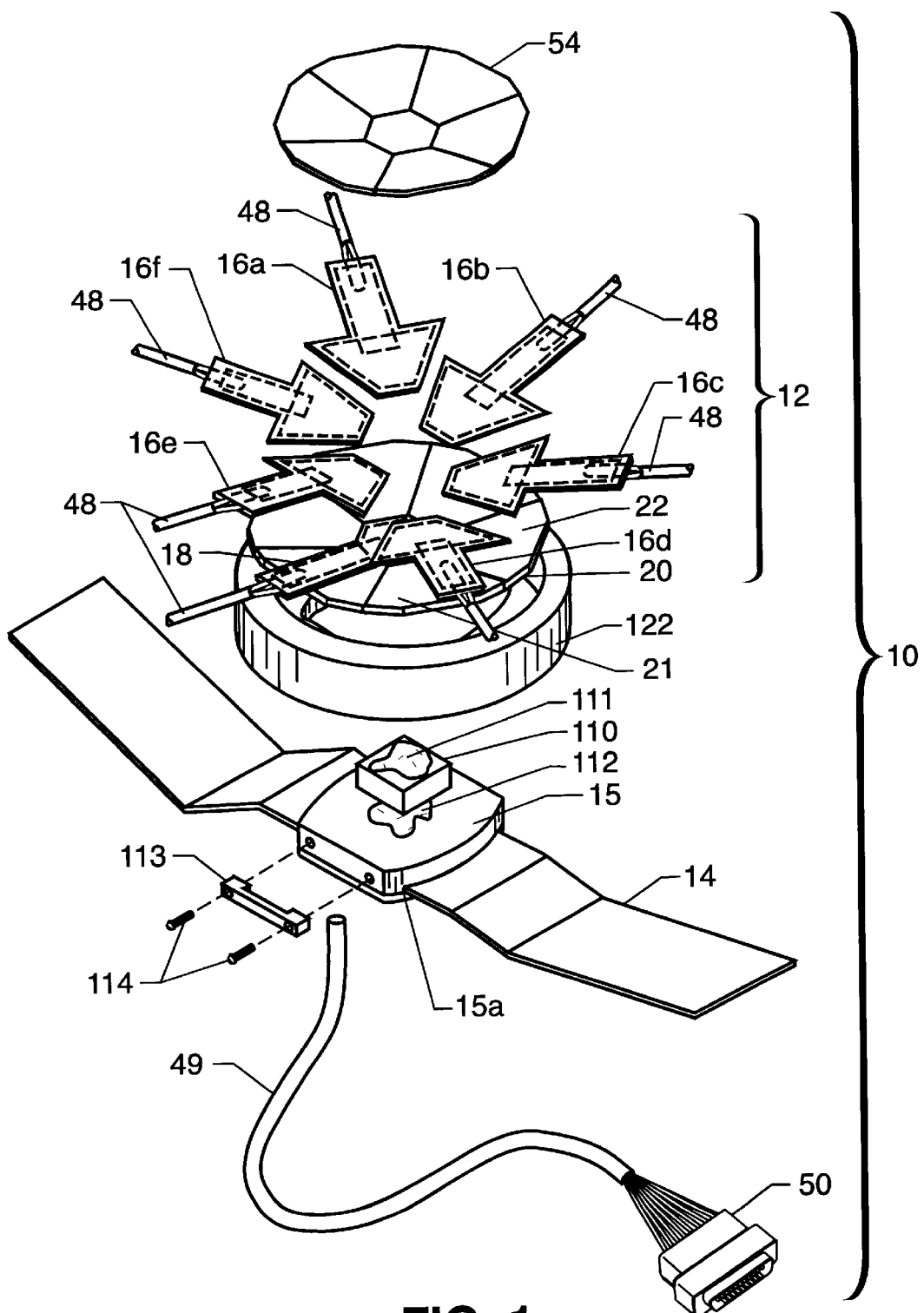
FIG. 1 is an exploded view of the fetal heart monitoring system of the present invention.
Figure 2:
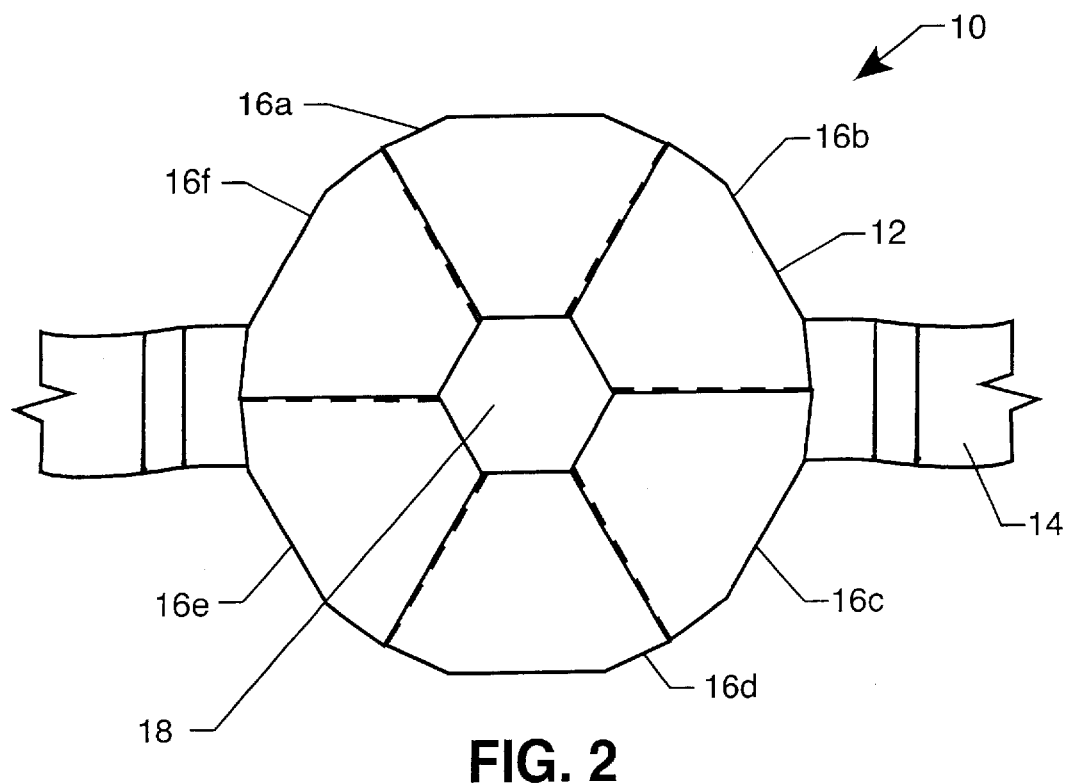
FIG. 2 is a plan view of the fetal heart monitoring system of FIG. 1.
Figure 3:
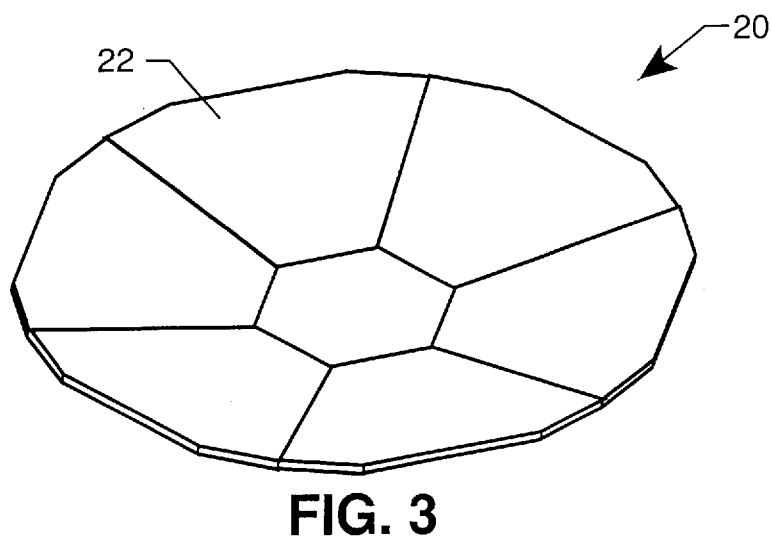
FIG. 3 is a perspective view of a backing plate shown in FIG. 1.

Referring to FIGS. 1 and 2, there is shown a fetal heart monitoring system 10 of the present invention. System 10 generally comprises sensor array 12. Sensor array 12 acquires acoustic signals emitted from a fetus inside a body. In one embodiment, system 10 further includes web belt 14 and web belt guide 15. Web belt guide 15 includes slot 15a that extends therethrough for receiving web belt 14. Sensor array 12 is attached to web belt guide 15. Web belt 14 is configured to be secured around the patient such that sensor array 12 confronts the exterior abdominal surface of the patient. Thus, the position of sensor array 12 relative to the patient can be adjusted by moving web belt guide 15 along web belt 14. Sensor array 12 comprises outer sensor elements 16a–16f, and inner sensor element 18. Sensor elements 16a–16f and 18 are ambulatory, non-invasive, passive fetal heart rate monitoring sensor elements. Sensor array 12 further comprises backing plate or support plate 20. Backing plate 20 has a generally concave front or top surface 22 and a generally convex back or bottom surface 23 (see FIG. 8) that is opposite top surface 22. Sensor elements 16a–16f and 18 are attached to concave surface 22. In one embodiment, sensor elements 16a–16f and 18 are bonded to top surface 22 with an adhesive film (not shown). In a preferred embodiment, sensor elements 16a–16f and 18 are attached to surface 22 in a manner such that the sensor elements conform to the concave contour of surface 22. The purpose and the particular geometrical shape of backing plate 20 are described in detail in the ensuing description.

Referring to FIG. 2, in one embodiment, each outer sensor 16a–16f has a generally trapezoidal shape and inner sensor 18 has a generally hexagonal shape. Other suitable shapes may be used as well.

Figure 4:
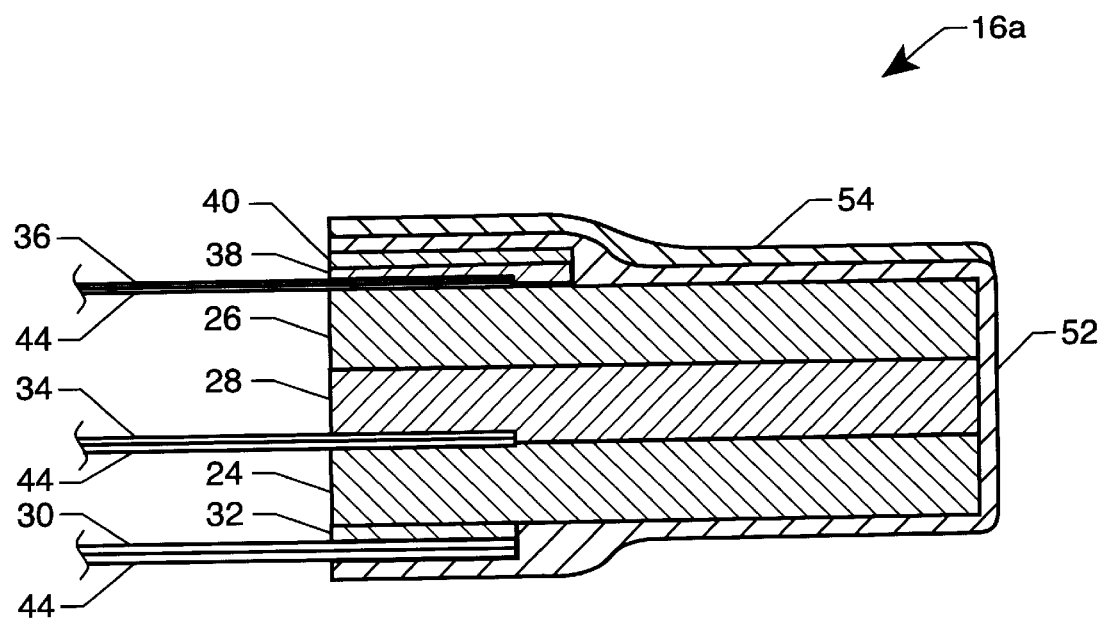
FIG. 4 is cross-sectional view of a sensor element shown in FIG. 1.

Referring to FIGS. 1 and 2, outer sensor elements 16a–16f are identically constructed. Therefore, for purposes of brevity, only outer sensor element 16a is described in the ensuing description. Referring to FIG. 4, sensor element 16a generally comprises piezoelectric polymer film layers 24 and 26 and electrically conductive adhesive layer 28. Film layer 24 can have a relatively thin metallic layer on each side thereof Similarly, film layer 26 can have a relatively thin metallic layer on each side thereof. Film layers 24 and 26 are bonded to each other with electrically conductive adhesive layer 28 to form a piezoelectric "bimorph." In one embodiment, electrically conductive adhesive layer 28 comprises an electrically conductive epoxy layer 28.

Referring to FIG. 4, sensor 16a further includes bottom outer electrode 30 that is bonded to piezoelectric layer 24 with electrically conductive adhesive 32, for example, a conductive epoxy layer 32. Sensor 16a further includes center electrode 34 that is positioned between piezoelectric film layer 24 and conductor epoxy layer 28. In one embodiment, epoxy layer 28 has a generally trapezoidal shape so as to provide sensors 16a with a generally trapezoidal shape as shown in FIG. 2. In other embodiments other shapes are possible, for example, in another embodiment an epoxy layer 28 has a generally triangular shape.

Figure 5:
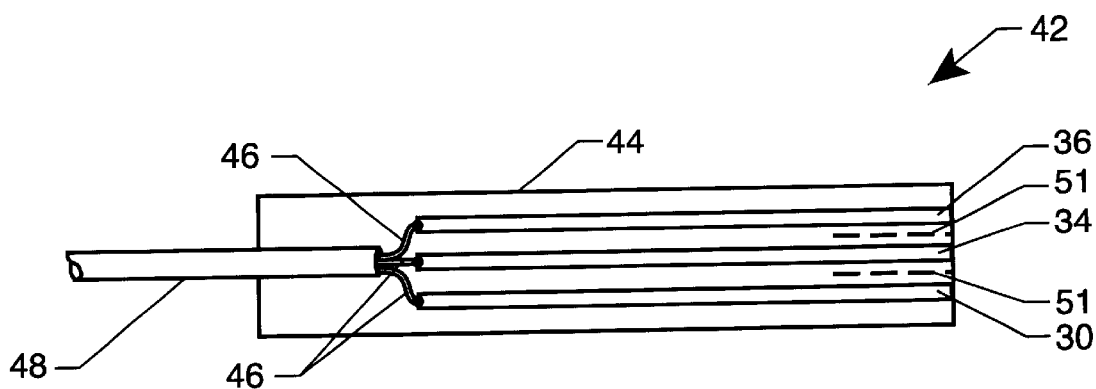
FIG. 5 is a plan view of a flex cable shown in FIG. 1.
Figure 6:
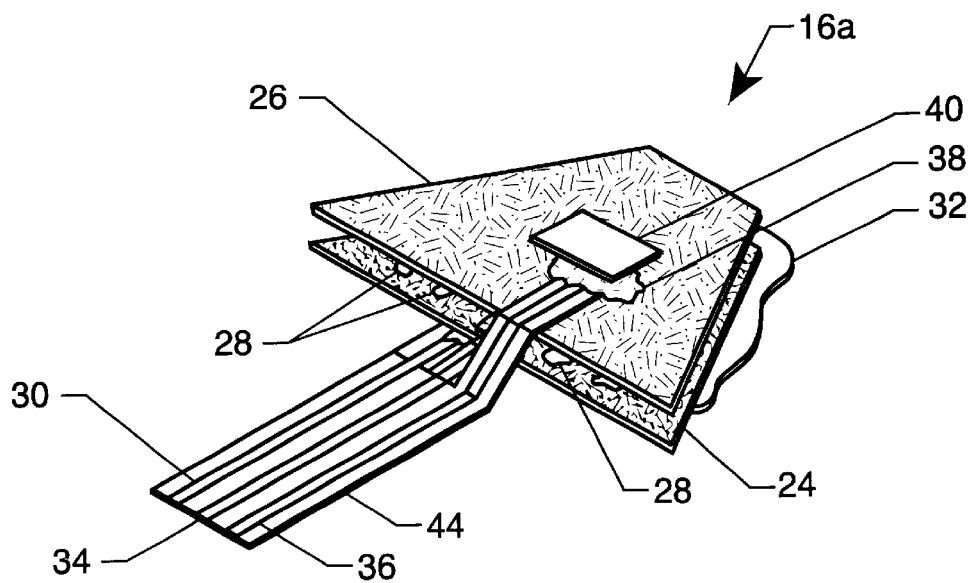
FIG. 6 is a perspective view of an outside sensor element shown in FIG. 1.

Referring to FIGS. 4, 5 and 6, sensor 16a further includes top outer electrode 36 that is bonded to piezoelectric film layer 26, for example, with conductive epoxy layer 38. Jumper tab or electrical connector patch 40, with its conductive side facing down, is disposed over epoxy layer 38. Jumper tab or electrical connector patch 40 facilitates attachment of top outer electrode 36 to piezoelectric film layer 26.

Referring to FIGS. 4, 5 and 6, in one embodiment, electrodes 30, 34 and 36 are part of a flex cable which can comprise a Upilex™ substrate having conductors, such as conductive traces, thereon that correspond to electrodes 30, 34 and 36. Such a flex cable is shown is FIG. 5. Flex cable 42 can comprise a Upilex™ substrate 44. As shown, conductive traces 30, 34 and 36 are formed on substrate 44. Conductive traces 30, 34 and 36 can be attached, such as by soldering, to corresponding wires 46 that extend through cable 48. Cable 48 extends through cable sleeve 49 (see FIG. 1). Wires 46 are electrically connected to corresponding contacts in connector 50 (see FIG. 1). Dashed lines 51 represent the areas where substrate 44 is cut in order to individually fold or bend the portions of substrate 44 having conductive traces 30, 34 and 36 thereon. This feature is described in the ensuing description of the method of making sensors 16a–16f and 18. Substrate 44 is relatively thin and flexible so as to conform to the concave and convex surfaces 22 and 23, respectively, of backing plate 20.

Referring to FIG. 4, sensor element 16a includes a shield 52 that substantially encapsulates piezoelectric layers 24 and 26 and epoxy layer 28. Shield 52 forms a "Faraday cage," as is known in the art, which, when grounded, provides an effective shield against electromagnetic interference. In one possible embodiment, shield 52 can be fabricated from copper clad Kapton™ film. In such an embodiment, the Kapton™ of the copper clad Kapton™ film can have a thickness of about 0.002 inch and can be laminated to a section of 1.0 ounce (0.0014 inch) copper foil with 0.0005 inch adhesive (this foil is positioned on the "outside" of the shield). Thus, the copper clad Kapton™ film has a total thickness of about 0.0039 inch. It is to be understood that the thickness of the copper clad Kapton™ film can be varied and need not be restricted to the aforementioned dimensions For example, the Kapton™ can have a thickness between about 0.0005 inch and 0.005 inch, and the copper foil can vary from about ¼ oz to 3.0 oz. Similarly, the thickness of the adhesive also can be varied. Additionally, other materials, such as polyimide materials with a high dielectric can also be used, e.g. Upilex™, Apical™, LaRC-SI, Thermalimide, etc. High-dielectric polyester films also can be used.

Shield 52 can be bonded to piezoelectric films 24 and 26, for example, with an adhesive layer (not shown). This feature is described in the ensuing description. Shield 52 permits relatively more intimate contact between sensor array 12 and the patient in comparison to utilizing just one common shield over all the sensor elements. Furthermore, shield 52 substantially reduces penetration by electromagnetic interference. For purposes of simplicity, shield 52 is not shown in FIG. 6.

Referring to FIGS. 1 and 4, sensor array 12 is covered by electrically non-conductive or insulating layer 54 that is disposed over the portion of shield 52 that covers piezoelectric layer 26. Layer 54 comes in contact with the external abdominal surface of the patient. Layer 54 electrically isolates sensor elements 16a–16f and 18 from the patient without compromising intimate contact between these sensor elements and the patient. Layer 54 can be made from a variety of suitable insultating material, for example, in one embodiment, layer 54 is fabricated from an electrically nonconductive high dielectric film (>6 KV/mil).

Referring to FIGS. 1 and 2, the particular structure of inner sensor element 18 is substantially the same as each of the outer sensors 16a–16f with the exception that the shape of inner sensor 18 is generally hexagonal.

It is to be understood that sensors 16a–16f can be configured to have shapes other than trapezoidal or hexagonal.

Figure 12:
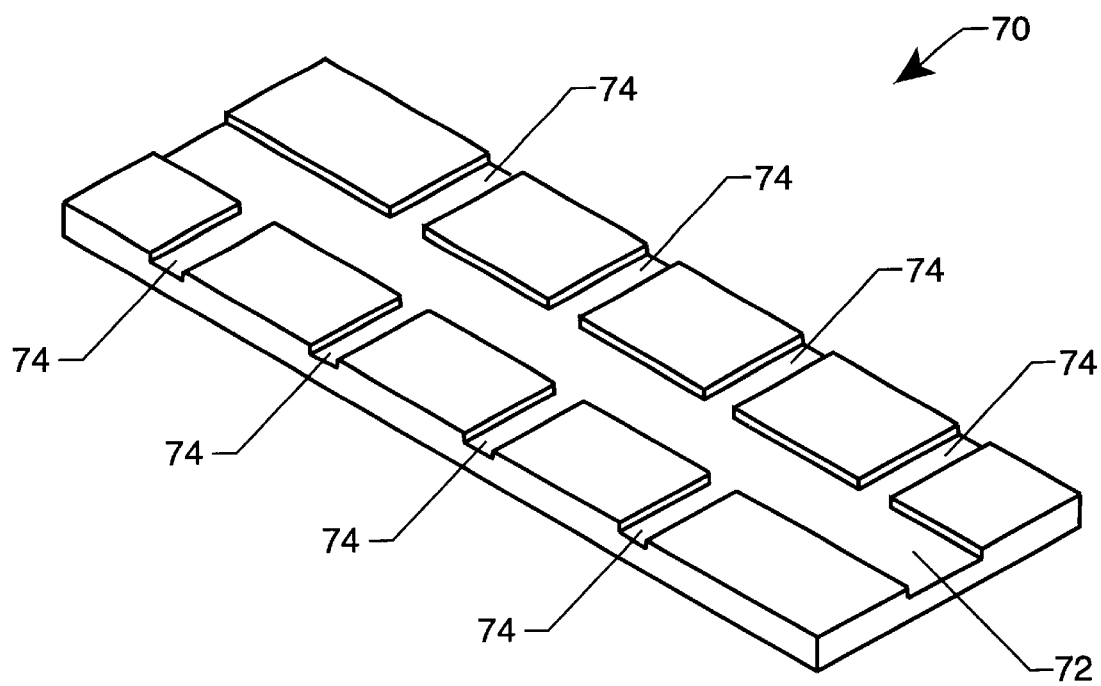
FIG. 12 is a perspective view of a fixture used for fabricating sensor elements in accordance with a method of the present invention.
Figure 13:
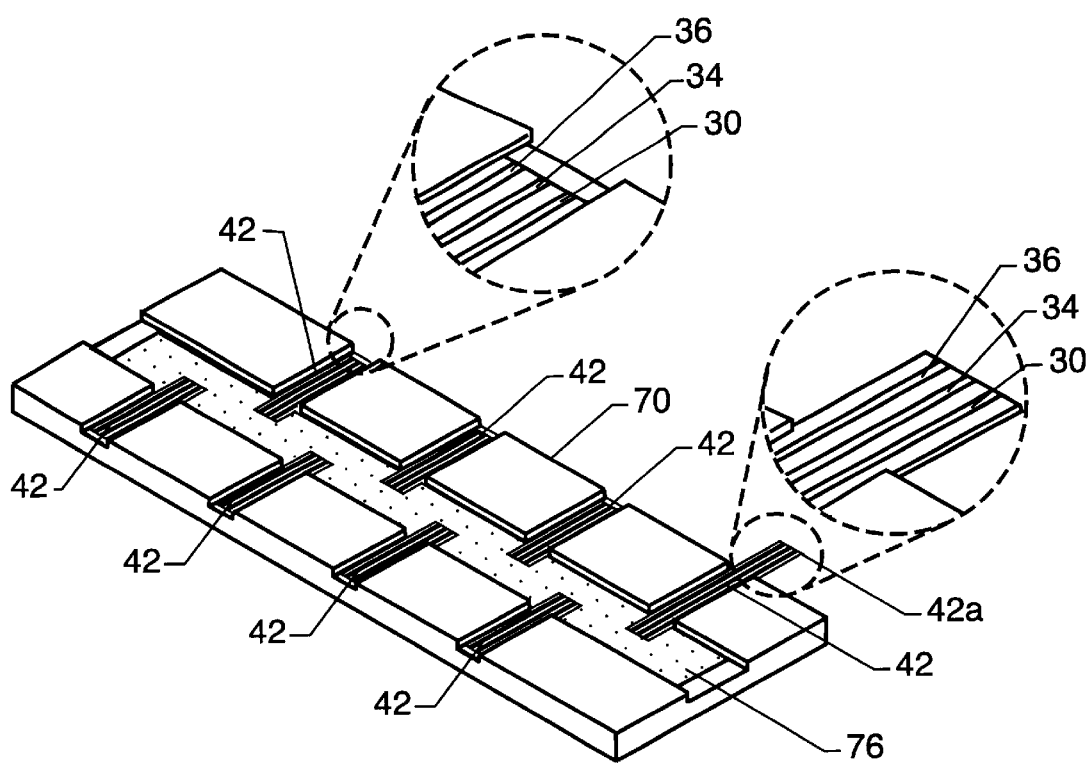
FIGS. 13–18 are views that illustrate pertinent steps of the method of fabricating sensor elements in accordance with the present invention.
Figure 14:
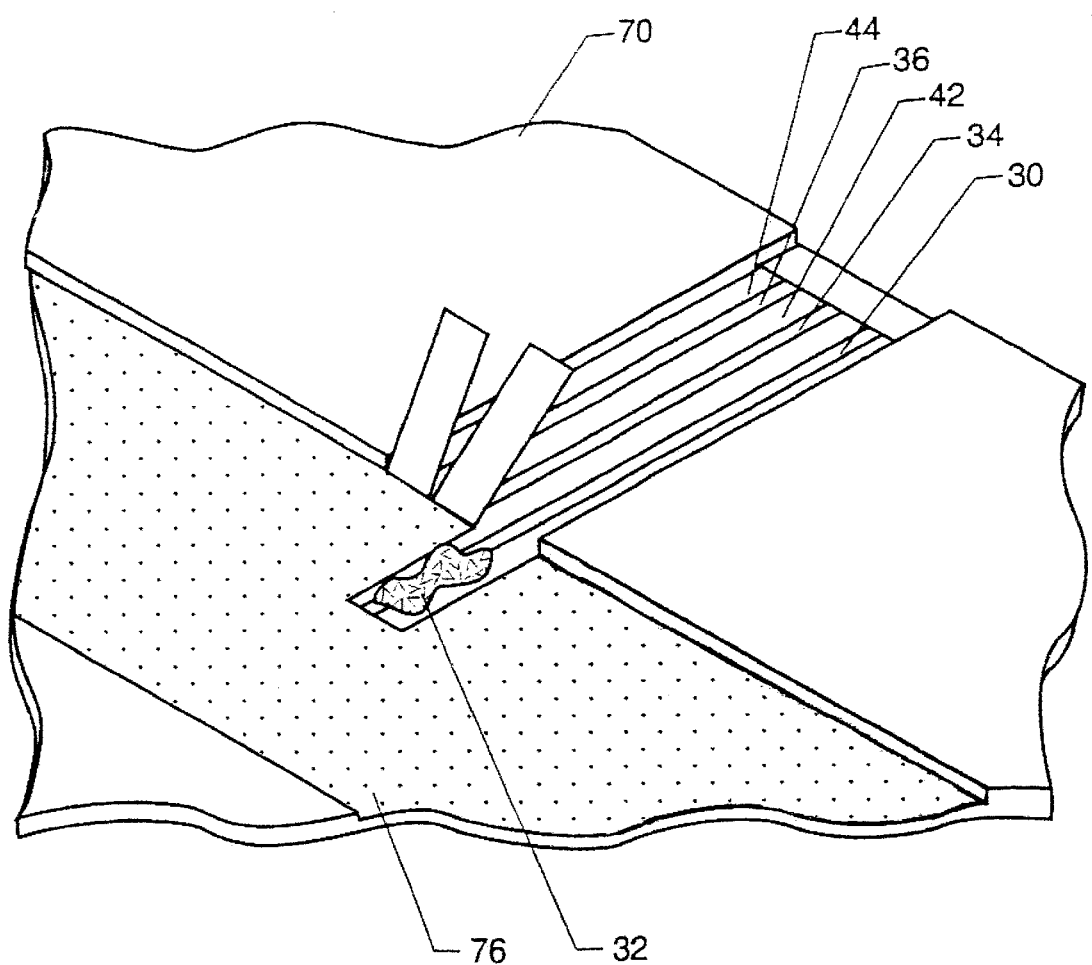
Figure 15:
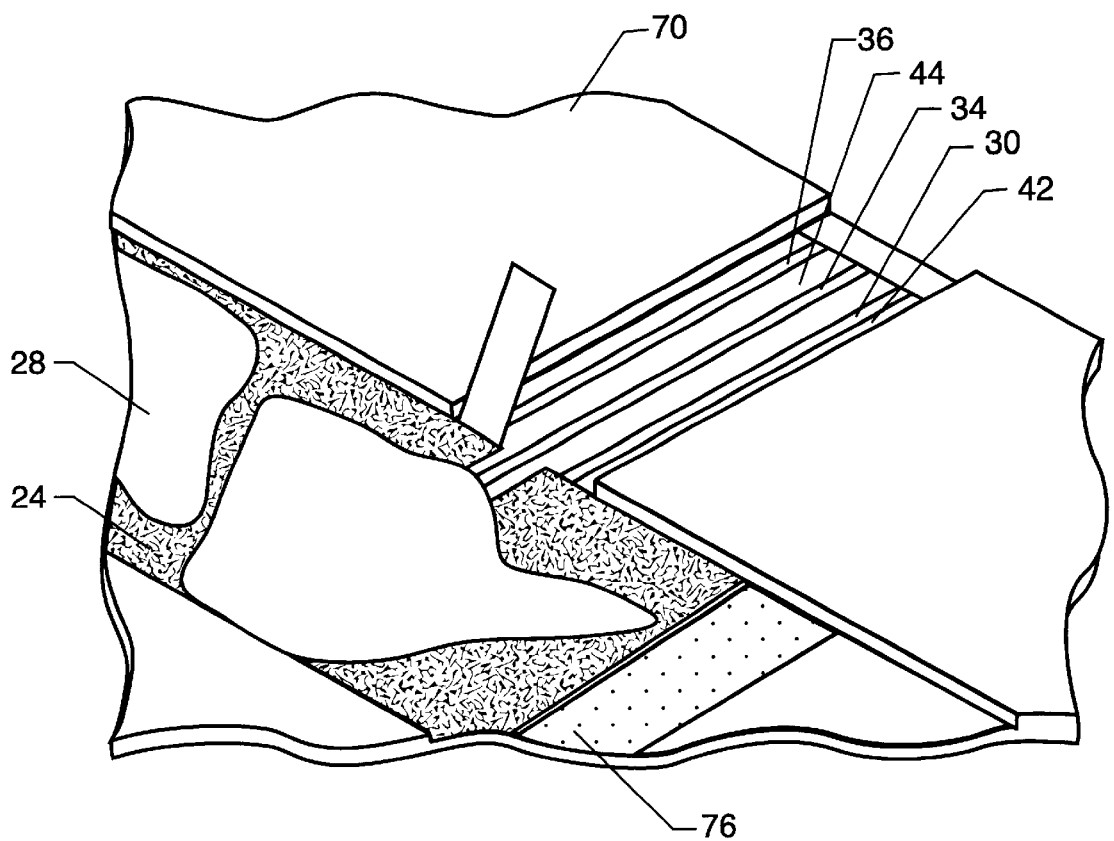
Figure 16:
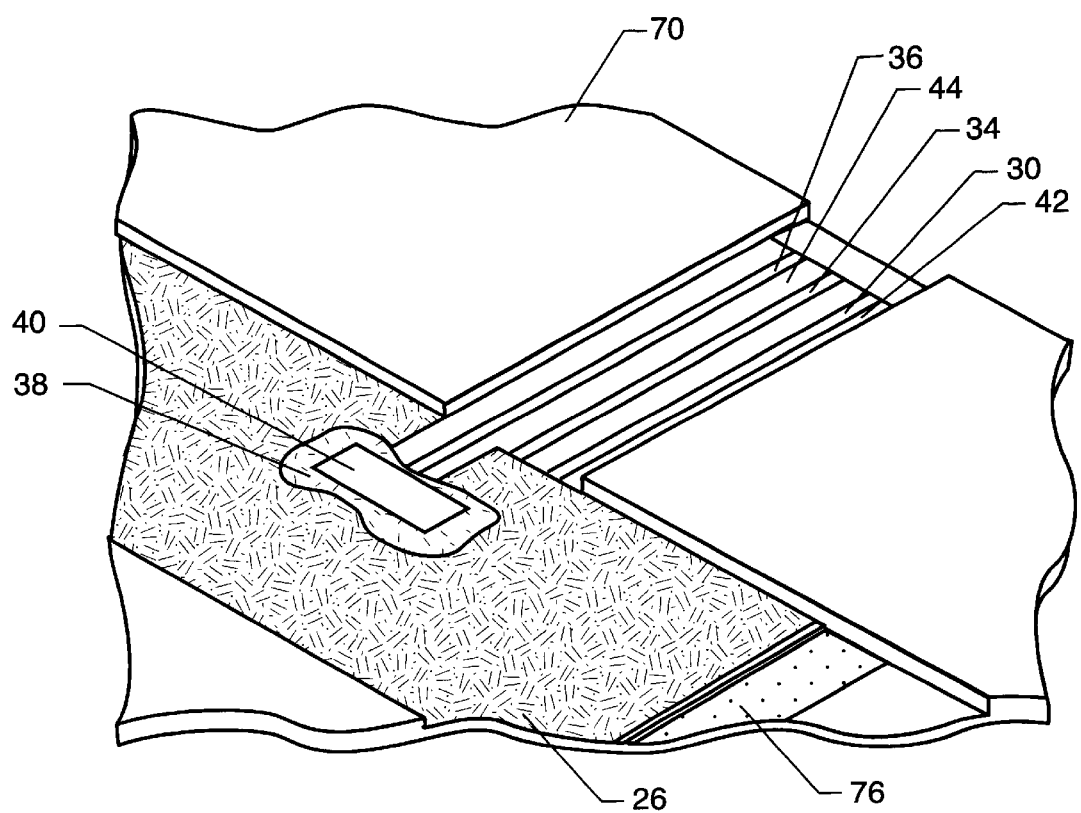
Figure 17:
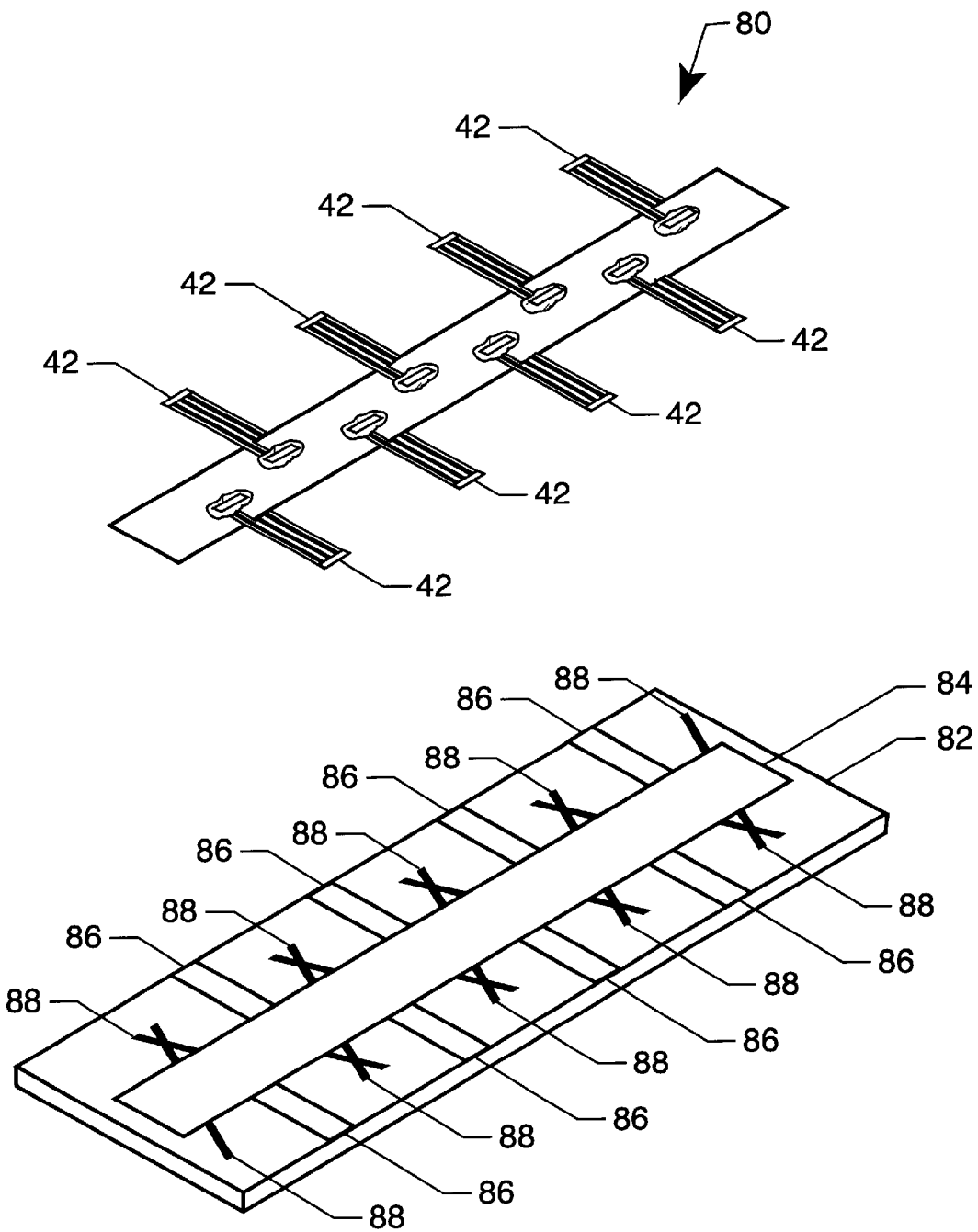
Figure 18:
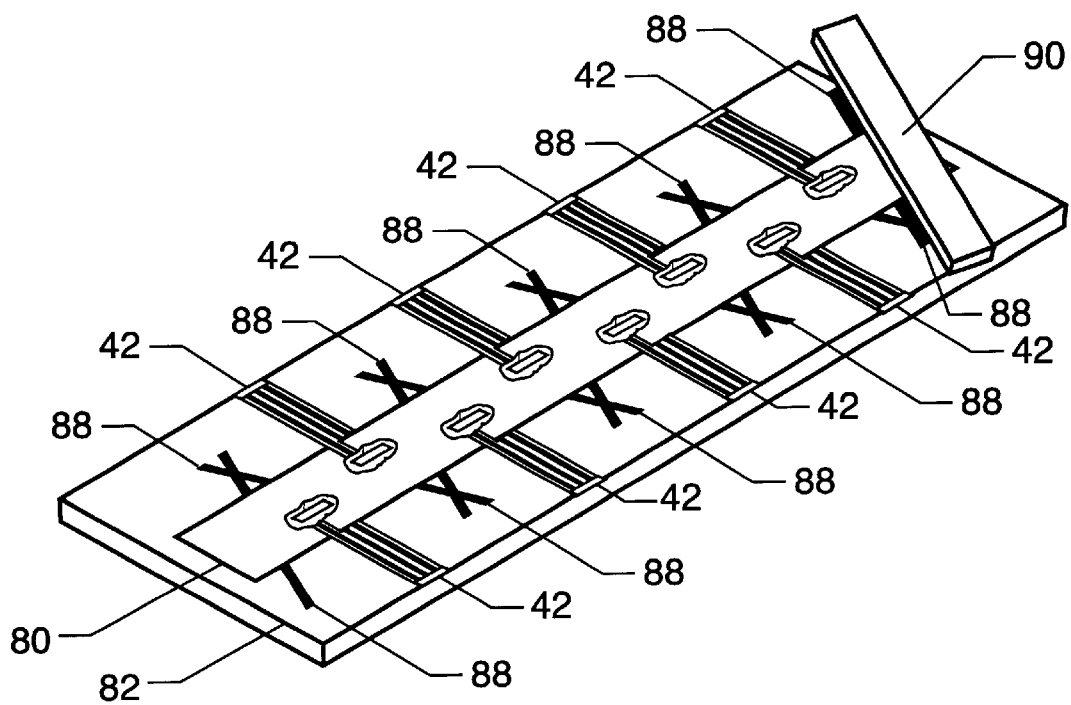
Figure 19A:
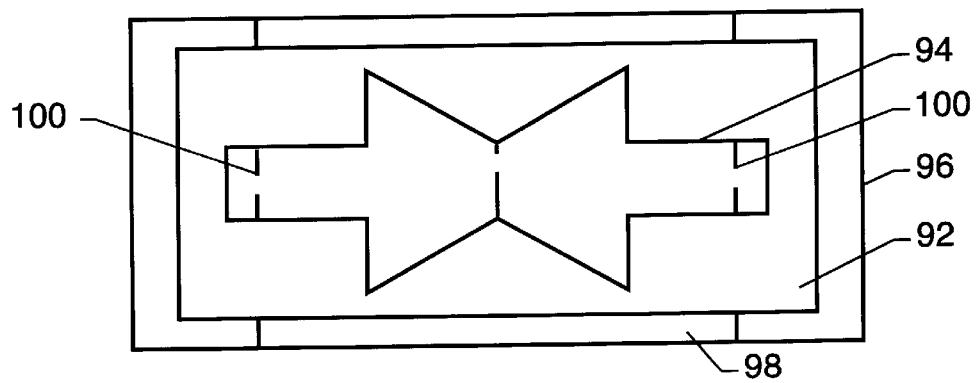
FIGS. 19A and 19B are plan views illustrating the fabrication of a shield that envelopes the sensor elements fabricated in accordance with the method of the present invention.
Figure 19B:
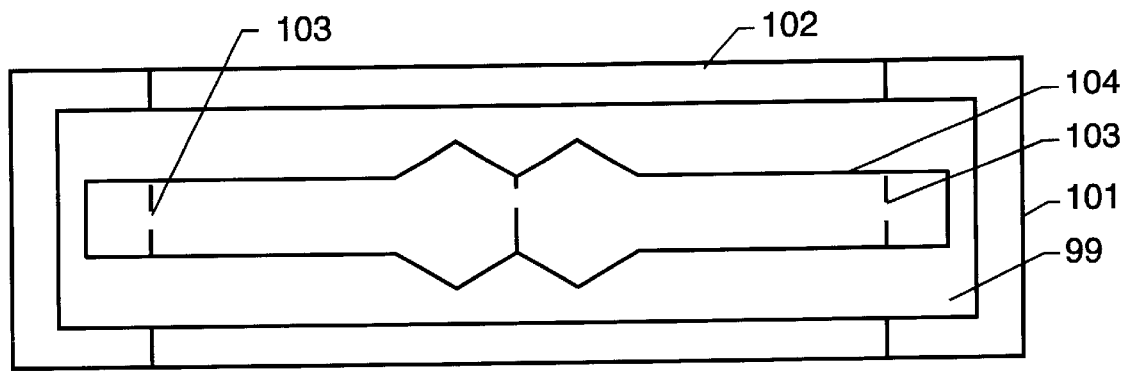

Each step of a preferred method of fabricating sensors 16a–16f and 18 is now explained in the ensuing description with reference being made to FIGS. 12–20.

a) The first step entails providing fixture 70 shown in FIG. 12. Fixture 70 includes main channel 72 and lateral channels 74.

b) Next, a release film cloth 76 is disposed within channel 72. In one embodiment, the release film cloth comprises a Teflon™ release film cloth such as the TFP-234 release film cloth.

c) In the next step, a plurality of flex cables 42 (see FIGS. 5 and 13) are disposed within lateral channels 74. A portion of each flex cable 42 extends over cloth 76. Each flex cable 42 has conductors (e.g. conductive traces) 30, 34 and 36. (see FIG. 5). Each flex cable 42 is cut to the appropriate length depending upon whether an outer sensor (e.g. sensor 16a) is being fabricated or an inner sensor (i.e. sensor 18) is being fabricated. For example, flex cable 42a is used for inner sensor 18 and thus, is longer than the other flex cables 42.

d) Next, each flex cable 42 is cut along dotted lines 51 (see FIG. 5) to allow the portions of substrate 44 having conductors 34 and 36 thereon to be folded or bent upward as shown in FIG. 14. The portion of substrate 44 having conductor 30 remains positioned over cloth 76. In one embodiment, tape is used to secure the portions of substrate 44 having conductors 34 and 36 thereon in the aforesaid particular positions.

e) Next, a layer of adhesive or material, such as layer 32 of conductive epoxy is disposed over conductor 30 as shown in FIG. 14, on each flex cable 42.

f) Referring to FIGS. 4 and 15, piezoelectric film 24 is then disposed within channel 72 and over cloth 76 and all layers of epoxy 32. Preferably, the polarity of piezoelectric film 24 is marked for purposes of identification. In a preferred embodiment, film 24 is positioned in a manner such that the (+) polarity faces upward. A template is used to cut the piezoelectric layer 24 into strips that are about 1⅛ inch wide.

g) Referring to FIG. 15, the portion of substrate 44 having conductor 34 thereon is bent downward so that it is above piezoelectric film 24. Conductive epoxy layer 28 (See FIG. 4) is then disposed over conductor 34. In a preferred embodiment, layer 28 has a generally trapezoidal shape to match the overall geometry of an outer sensor (i.e sensors 16a–16f). On the other hand, if the sensor being fabricated is inner sensor 18, then it is preferred that layer 28 have a generally hexagonal shape.

h) Next, second piezoelectric layer 26 is then disposed within channel 72 and over all epoxy layers 28. In a preferred embodiment, layer 26 is disposed in such a manner that the (+) polarity side faces downward and confronts and contacts the (+) polarity side of piezoelectric layer 24.

i) In the next step, the portion of substrate 44 having conductor 36 thereon is unfolded or bent downward so that it is disposed over piezoelectric layer 26 as shown in FIG. 16, on each flex cable 42.

j) Next, conductive adhesive or material, such as epoxy layer 38 is disposed over conductor 36 as shown in FIG. 16, on each flex cable 42.

k) The next step entails disposing jumper tab or electrical connector patch 40 over conductive epoxy layer 38 as shown in FIGS. 4 and 16, on each flex cable 42. Jumper tab or electrical connector patch 40 facilitates electrical connection between conductor 36 and epoxy layer 38.

l) Next, a stainless steel strip (not shown) is disposed within channel 72 and over piezoelectric layer 26, each epoxy layer 38 and each jumper tab 40.

m) A piece of release cloth (not shown) is then disposed over the stainless steel strip and a substantial portion of each flex cable 42.

n) In the next step, fixture 70 as well as the components thereon are covered with a bleeder cloth, for example made from fiberglass (not shown).

o) The fixture, component and bleeder cloth are preferably placed in a vacuum bag to allow the epoxy to cure so as to form a cured, multi-sensor laminate assembly 80 (see FIG. 17). In a preferred embodiment, the temperature during the cure process does not exceed 80° C.

p) Referring to FIG. 17, cured laminate assembly 80 is removed from the vacuum bag, it is placed on template 82 which is secured to a cutting surface (not shown). Template 82 has indicia or markings 84 and 86 for aligning assembly 80 on template 82. Template 80 further includes indicia or markings 88 that provide a guide for cutting laminate assembly 80 to form individual sensors.

q) Referring to FIG. 18, a cutting device (not shown), such as a razor blade, is used in conjunction with straight edge 90 to cut laminate assembly 80 along indicia or markings 88.

r) Referring to FIGS. 4, 19A and 19B, the next step entails forming individual shields 52 for each sensor. FIG. 19A illustrates the arrangement of materials for fabricating shield 52 for each outer sensor 16a–16f. FIG. 19B illustrates the arrangement of materials for fabricating shield 52 for inner sensor 18. Referring to FIG. 19A, a template, such as paper template 92 is used to fabricate a shield 52 for each of the outer sensors 16a–16f. Template 92 has indicia or markings 94 thereon to function as cutting guides. Template 92 is placed on a blank 96, which in one embodiment can be a copper clad Kapton™ blank 96. Kapton™ blank 96 can have adhesive film 98 thereon. Template 92 includes indicia or markings 100 to facilitate alignment of template 92 on adhesive film 98. Adhesive film 98 can have release paper on both sides thereof. The release paper on one side of film adhesive 98 is removed so the corresponding side of film 98 can be adhered to Kapton™ blank 96. Template 92 is placed over the other side of adhesive 98 which still retains its corresponding release paper. A cutting instrument, e.g. scissors, razor, etc. is used to cut along markings 94 to produce shield 52 for one of the outer sensors 16a–16f.

Figure 20:
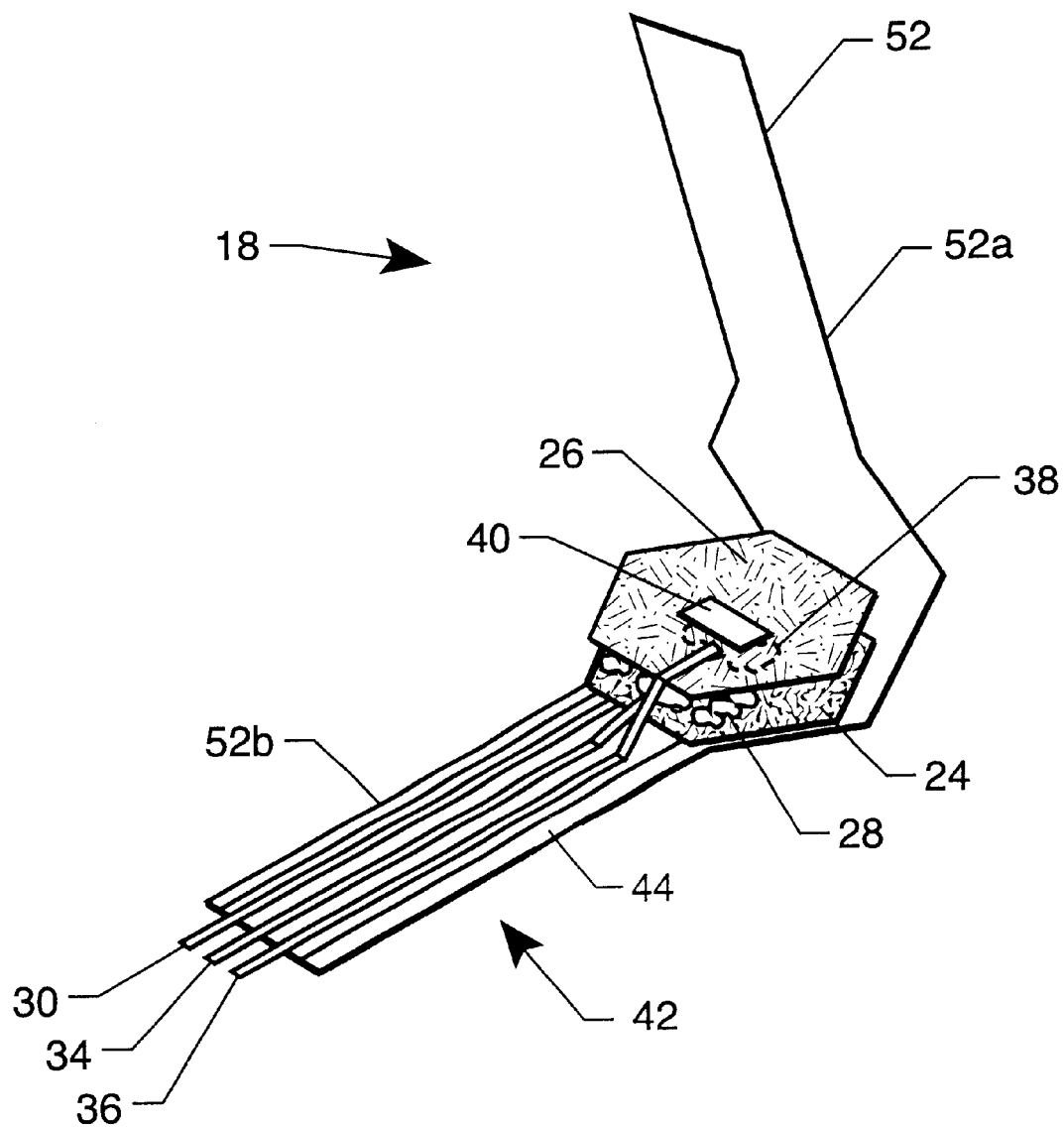
FIG. 20 is a perspective view illustrating the attachment of the shield, made according to FIG. 19B, to an inner sensor element that was made in accordance with the method of the present invention.

Similarly, referring to FIG. 19B, paper template 99 is used to fabricate a shield 52 for the inner sensor 18. Template 99 has indicia or markings 104 thereon to function as a cutting guide. Template 99 is placed on copper clad Kapton™ blank 101. Kapton™ blank 101 has adhesive film 102 thereon. Template 99 includes indicia or markings 103 to facilitate alignment of template 99 on adhesive film 102. Adhesive film 102 has release paper on both sides thereof The release paper on one side of film adhesive 102 is removed so that side of film adhesive 102 can be adhered to Kapton™ blank 101. Template 99 is placed over the other side of adhesive film 102 which still retains its corresponding release paper. A cutting instrument, e.g. scissors, razor, etc. is used to cut along markings 100 to produce shield 52 for inner sensor 18.

s) Referring to FIG. 20, there is shown inner sensor element 18 fabricated in accordance with the method described in the ensuing steps and prior to installation of shield 52. Shield 52 has portions 52a and 52b. Portion 52a is partially folded or bent upward. The adhesive film release paper on portion 52b is removed and sensor element 18 is disposed over and adhered to the exposed portion of the adhesive film. Once sensor element 18 is adhered to the adhesive film, the adhesive film release paper is removed from portion 52a. Shield portion 52a is then pressed down so that the adhesive film adheres to piezoelectric layer 26, epoxy layer 38 and jumper tab 40 (see also FIG. 16).

The method described above results in a plurality of sensor elements being fabricated simultaneously without wasting materials.

Referring to FIGS. 1, 2 and 4, electrically insulating layer 54 is disposed over all sensors 16a–16f and 18 with an adhesive film layer (not shown). In one embodiment, insulating layer 54 is a polyimide film insulator layer One such polyimide layer is the LaRC-SI (Langley Research Center-Soluble Imide) polyimide film. An adhesive film layer (not shown) is used to adhere insulating layer 54 to the sensors 16a–16f and 18. In another embodiment, electrically insulating layer 54 comprises a conformal coating. In a further embodiment, insulating layer 54 comprises Kapton™ tape. Electrically insulating layer 54 contacts the external maternal abdominal surface and electrically isolates sensor array 12 from the patient without comprising intimate sensor contact with the maternal abdominal surface.

The ensuing description describes the particular structural details of system 10 with reference being made to FIGS. 1, 2, 3, and 7–11A. As described in the foregoing description, backing plate 20 is configured so as to have perimetrical edge 21, concave surface 22 and convex surface 23. Backing plate 20 can be made from a variety of suitable materials, such as aluminum or steel. In one embodiment, backing plate 20 is fabricated from brass. In one embodiment, backing plate 20 is about 1/16 inch thick. Backing plate 20 serves as an acoustical sounding board for the pressure pulses emanating from the fetal heart. Backing plate 20 provides a relatively high acoustical impedance and thereby reflects substantially all the incident pressure back into the maternal abdomen. As a result, the superposition of the incident and reflected pressures nearly doubles the pressure amplitude at the surface of backing plate 20 thereby improving the signal gain.

Figure 7:
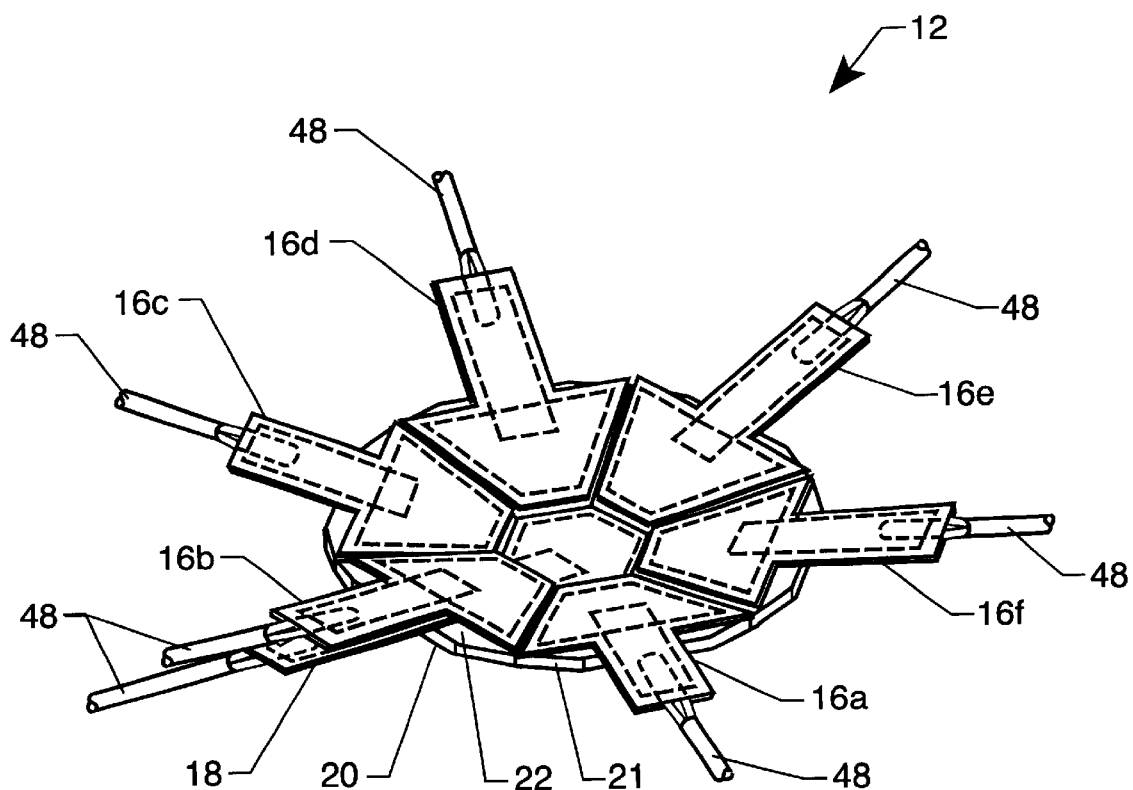
FIG. 7 is a perspective view of the backing plate of FIG. 3 having the sensor elements shown in FIG. 1 attached thereto.

As shown in FIG. 7, outer sensor elements 16a–16f and inner sensor element 18 are bonded to concave surface 22 of backing plate 20 with an adhesive (not shown) to form sensor array 12. Sensor element 16b is bonded over a portion of inner sensor element 18. In one embodiment, the adhesive used to bond sensor elements 16a–16f and 18 to backing plate 20 is an RTV (room temperature vulcanizing) adhesive. As shown in FIG. 2, inner sensor element 18 is surrounded by outer sensor elements 16a–16f. In a preferred embodiment, backing plate 20 is substantially rigid so as to retain sensors 16a–16f and 18 in fixed locations thereby substantially eliminating detection of acoustic signals associated with movement or vibrations of sensors, a problem common with prior art device. Thus, when system 10 is in use, essentially only the fetal heart tones, in conjunction with external filtering, are detected.

As shown in FIG. 7, sensors 16a–16f conform to the contour of concave surface 22. The concave contour of surface 22 and the position of sensors 16a–16f and 18 on surface 22 conforms to the contour of the external maternal abdominal surface and provides a region for receiving a portion of the exterior abdominal surface of the patient. Such a configuration provides intimate contact between sensors 16a–16f and 18 and the aforementioned exterior abdominal surface thereby significantly improving detection of the fetal heart tones.

Figure 8:
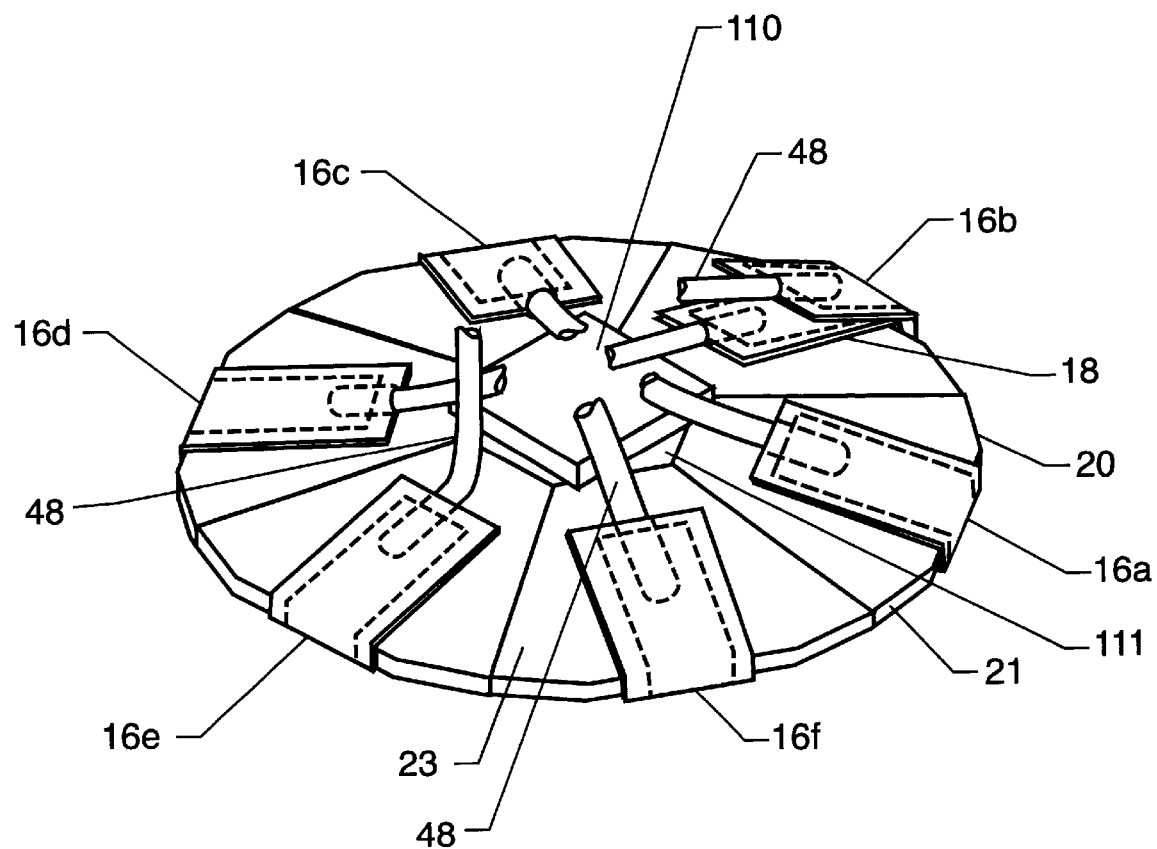
FIG. 8 is a perspective view illustrating the manner in which the sensor elements, shown in FIG. 7, are folded about a perimetrical edge of the backing plate shown in FIG. 7.
Figure 9:
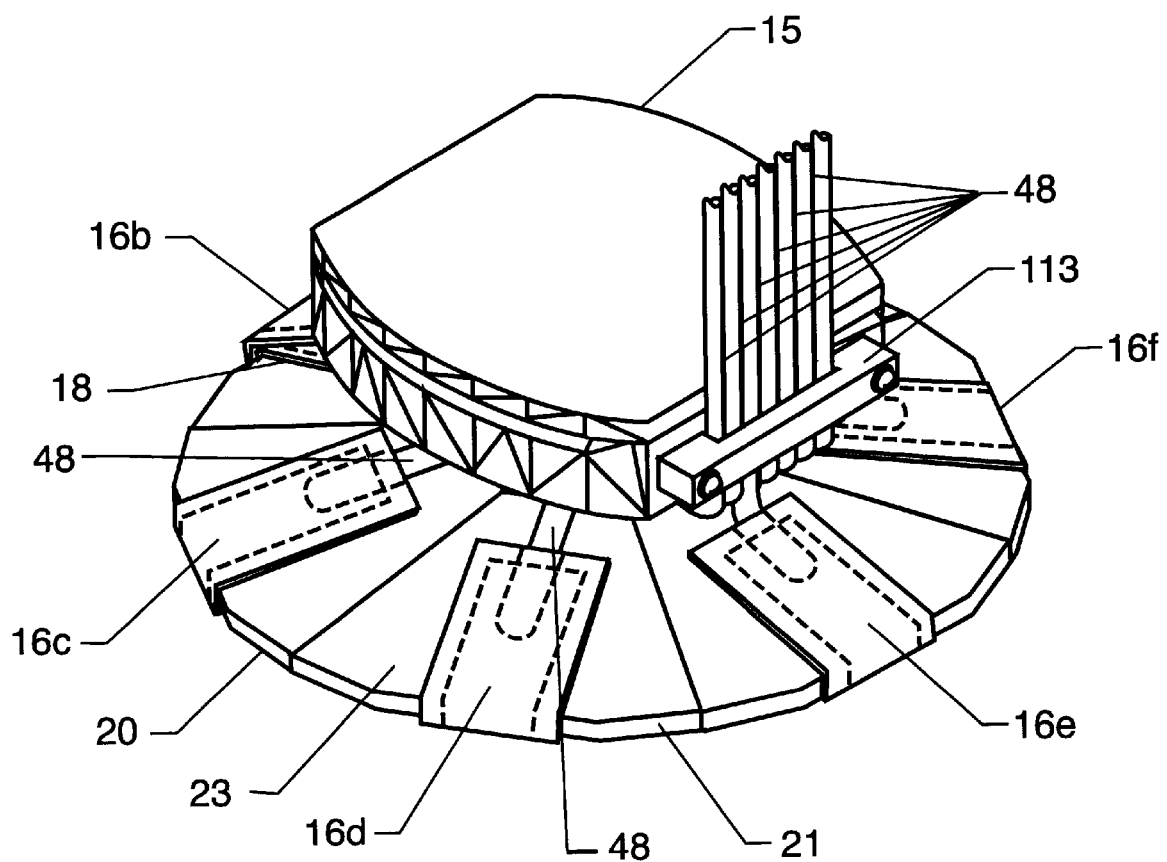
FIG. 9 is a perspective view illustrating the attachment of a web belt guide and a cable clamp, both of which being depicted in FIG. 1, to the assembly shown in FIG. 8.

Referring to FIGS. 8 and 9, spacer block 110 is bonded to the central portion of surface 23 of backing plate 20, such as with epoxy 111. In a preferred embodiment, spacer block 110 is electrically non-conductive. The portions of sensors 16a–16e that extend beyond perimetrical edge 21 are folded over perimetrical edge 21 so that such portions of the sensors contact and confront convex surface 23 of backing plate 20 (see FIG. 8). Web belt guide 15 is bonded to spacer block 110 with epoxy 112, for example. Referring to FIGS. 1, 8 and 9, cable clamp 113 is removably attached to web belt guide 15 with screws 114. Cables 48 are routed around spacer block 110 and through cable clamp 113. Cable sleeve 49 is fitted over cables 48. The conductors of cables 48 are electrically connected to contacts in electrical connector 50. Electrical connector 50 is configured for connection to signal processing equipment for detection and processing of fetal heart tones.

Figure 10:
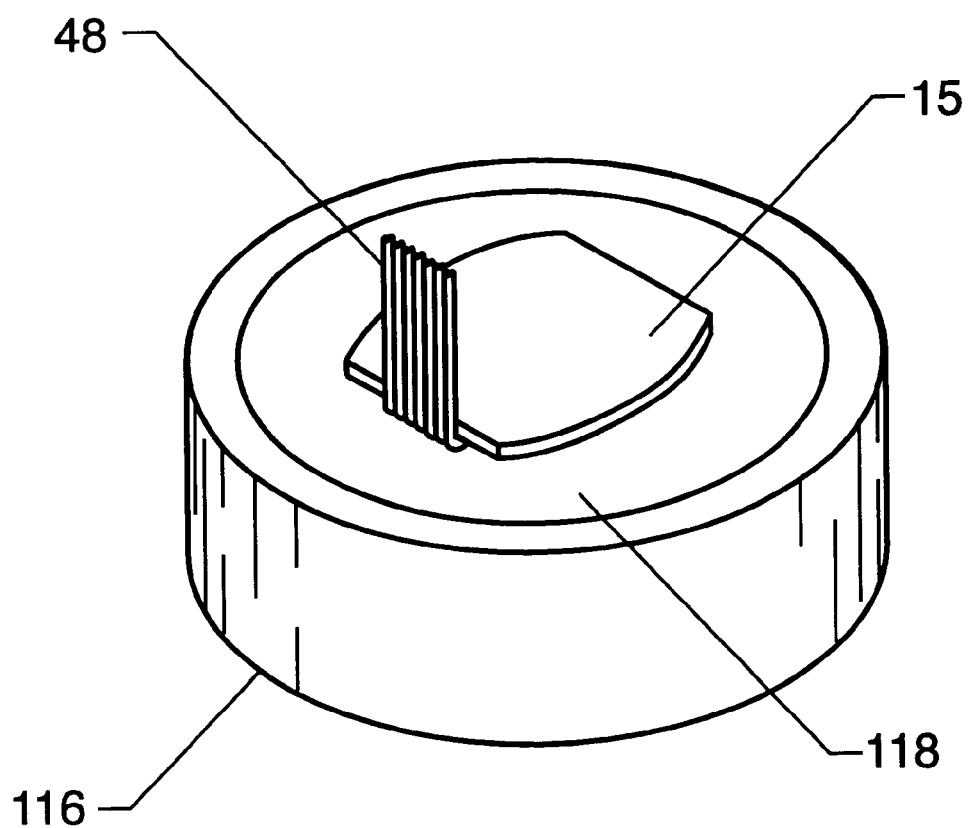
FIG. 10 is a perspective view illustrating the assembly of FIG. 9 positioned within a potting mold.
Figure 11:
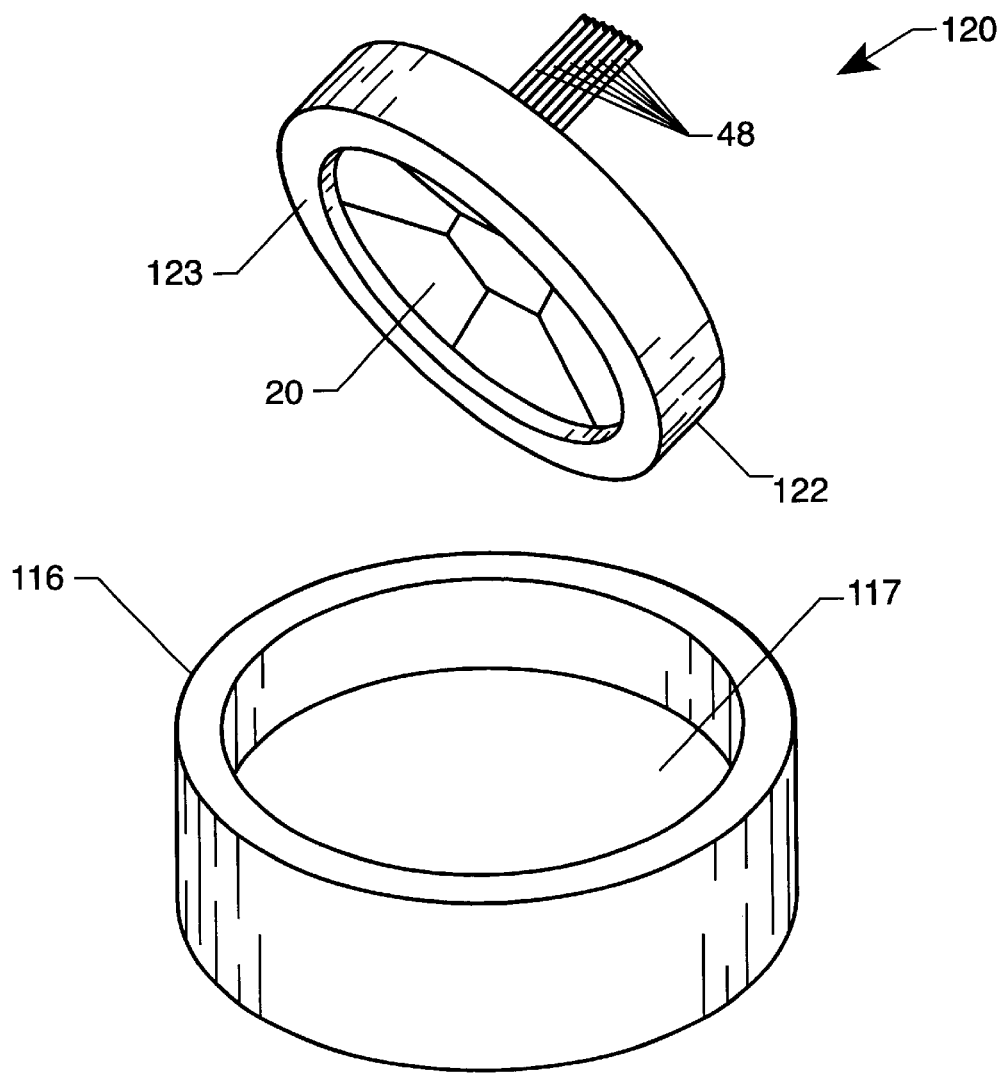
FIG. 11 is an exploded view illustrating the removal of a potted sensor assembly from the potting mold.
Figure 11A:
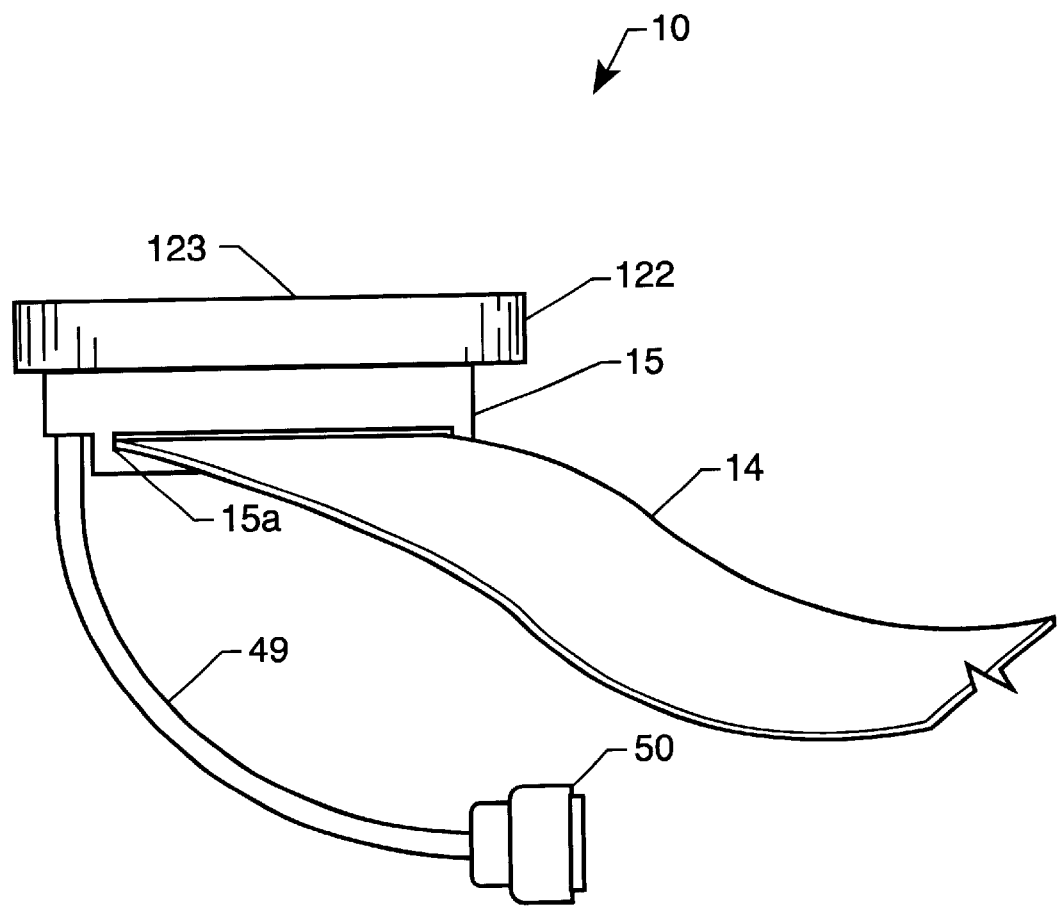
FIG. 11A is a side elevational view of a completed fetal heart monitoring system of the present invention.

After the structure shown in FIG. 9 is formed, a dam, such as a clay ring (not shown) is placed on concave surface 22 (see FIG. 7) adjacent to perimetrical edge 21. Referring to FIGS. 10 and 11, the structure shown in FIG. 9, with the clay ring attached thereto, is then placed inside mold 116. The clay ring contacts bottom surface 117 of mold 116 but prevents any part of concave surface 22 from contacting surface 117. Potting material, such as RTV potting material 118, is then poured into mold 116 such that cable clamp 113 (see FIG. 9) is completely covered with RTV potting material 118. The RTV potting material 118 is then cured in accordance with manufacturer's specifications. Referring to FIG. 11, positive air pressure is injected into a blowhole (not shown) on the underside of mold 116 to facilitate removal of RTV potted sensor assembly 120 from mold 116. Assembly 120 includes annular RTV potting structure 122 that has a perimetrical edge 123 The clay ring (not shown) is then removed from concave surface 22 of backing plate 20. Web belt 14 is then inserted through the slot 15a of web belt guide 15 thereby providing completed fetal heart monitoring system 10 as shown in FIG. 2 and FIG. 11A.

In one embodiment, RTV potting material 118 is medical grade RTV which has a relatively high tear strength. Such a medical grade RTV potting material 118 is the commercially available RTV 630A or 630B which are manufactured by General Electric. These particular types of RTV potting materials form a solid and durable potting structure upon congealing. Referring to FIG. 11, RTV potting structure 122 seals around perimetrical edge 21 of backing plate 20 and provides a space between perimetrical edge 21 of backing plate 20 and perimetrical edge 123 of potting structure 122. Thus, RTV potting structure 122 provides electrical insulation between the perimetrical edge 21 of backing plate 20 and the patient. RTV potting structure 122 also provides structural integrity for sensor array 12, holds backing plate 20 to web belt guide 15, and increases the overall weight of system 10 thereby facilitating good physical contact with the external maternal abdominal surface. In alternate embodiments different material could be used, for example a plastic shell or cap, or molded compound could be used in place of the RTV potting material. In at least one embodiment, if deemed desirable, the plastic cap could be weighted.

Referring to FIG. 2, system 10 is used in a manner such that web belt 15 is fastened to the patient such that sensor array 12 is applied to the external maternal abdominal surface and sensors 16a–16f and 18 are pressed against the maternal abdominal surface. Sensor array 12 is then adjusted with respect to the patient by sliding sensor array 12 along web belt 14. Sensor array 12 converts the incident pressure pulses from the fetal heart into electrical signals which are transmitted over the conductors of cables 48.

Figure 21A:
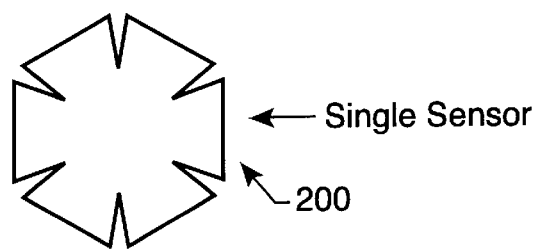
FIG. 21A illustrates one possible embodiment for a single sensor element.
Figure 21B:
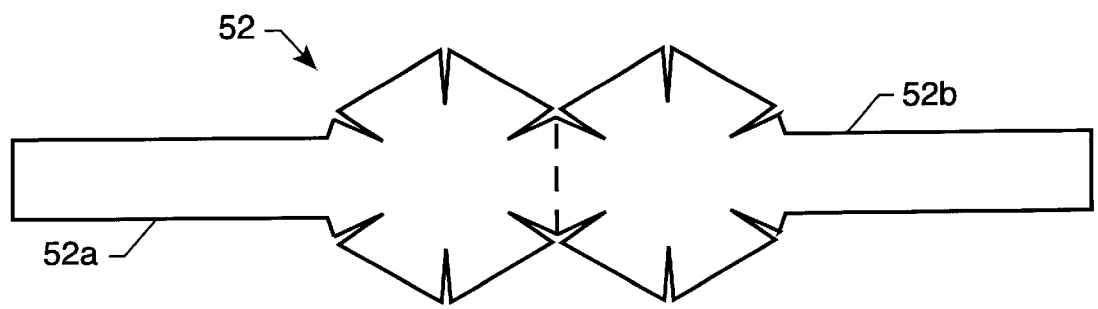
FIG. 21B illustrates a shield that could be utilized in conjunction with the single sensor element embodiment shown in FIG. 21A.

In reference to FIGS. 21A and 21B, in alternate embodiments, sensor array 12 can be configured to utilize a single sensor element 200. This element can be of a variety of possible shapes, and can be curved or flat. Preferably this sensor has a shape, that conforms to the concave surface 22 of backing plate 20. One possible shape for this single sensor is shown in FIG. 21A. When one sensor is used the backing plate 20 previously described can be used or in at least one alternative embodiment the backing plate 20 can be reconfigured to complement the shape and size of the single sensor 200. Similarly, as shown in the embodiment shown FIG. 21B, the shield 52 can also be configured to compliment the single sensor size and shape. The method and materials for making, as well and the function of this single sensor are essentially the same as disclosed above for the multi-sensor system.

In another embodiment, web belt 14 and web belt guide 15 are not used. For example, in one such embodiment, a user may grasp RTV potting structure 122 and place sensor array 12 against the external abdominal surface of the patient.

Thus, system 10 of the present invention provides the following advantages and benefits that address the problems associated with the conventional fetal heart monitoring systems:

a) Backing plate 20 serves as a sounding board thereby increasing the signal amplitude from the fetal pressure pulses. Backing plate 20 also offers a high acoustic impedance to the incident pressure pulses.

b) The concave contour of surface 22 of backing plate 20 facilitates improved intimate contact with the maternal abdominal surface resulting in greatly improved detection of the fetal heart tone.

c) The individual shielding of sensors 16a–16f and 18 with shield 52 minimizes electromagnetic radiation noise from external sources as well as acoustical noises from the shielding itself. Each individual shield 52 is bonded to each sensor element thereby eliminating crackling of the single piece-copper shield used in most prior art devices.

d) Flex cables 42 afford a modular method of effecting electrical connections that are substantially flush and non-intrusive.

e) RTV potting structure 122 holds web belt 14 in fixed position with slight pressure, thereby facilitating detection of acoustic fetal heart tones and eliminating detection of noise.

f) The thin film high dielectric external insulating layer 54 electrically isolates sensor array 12 from the patient without compromising intimate sensor contact.

An example of an interface for fetal heart monitoring which can be used with the present invention can be found in U.S. patent application Ser. No. 09/784,413 now U.S. Pat. No. 6,551,251 being contemporaneously filed with the instant patent application on Feb. 13, 2001, entitled "Passive Fetal Heart Monitoring System" with inventors: A. Zuckerwar and D. Mowrey. This application is hereby incorporated by reference as if set forth in its entirety herein.

The principals, preferred embodiments and modes of operation of the present invention have been described in the foregoing specification. The invention which is intended to be protected herein should not, however, be construed as limited to the particular forms disclosed, as these are to be regarded as illustrative rather than restrictive. Variations or changes may be made by those skilled in the art without departing from the spirit of the invention. For example, the numbers, size and shape of the sensors may vary. Additionally, materials may vary from those specified above. For example, insulating materials can include a variety of suitable materials, such as polymers, plastics, RTV compounds, etc. Likewise, different types or methods of bonding might be used as appropriate, during different steps of the disclosed method, such as, welding, riveting, melting, etc. Accordingly, the foregoing detailed description should be considered exemplary in nature and not limited to the scope and spirit of the invention as set forth in the attached claims.

Thus, having described the invention, what is claimed is:

1. A fetal heart monitoring system, comprising:
   a backing plate having a front surface and a back surface;
   at least one sensor element for acquiring acoustic fetal heart signals produced by a fetus within a body;
   the at least one sensor element being attached to the backing plate solely on the front surface; and
   the front surface being configured to be disposed to face toward the body when the attached at least one sensor element is positioned for acquiring the fetal heart signals.

2. The fetal heart monitoring system according to claim 1 wherein the at least one sensor element has a shape that conforms to the front surface of the backing plate.

3. The fetal heart monitoring system according to claim 1 wherein the at least one sensor element comprises:
   an inner sensor element; and
   a plurality of outer sensor elements surrounding the inner sensor element.

4. The fetal heart monitoring system according to claim 3 wherein the inner sensor element has a generally hexagonal shape and each of the outer sensor elements has a generally trapezoidal shape.

5. The fetal heart monitoring system according to claim 1 further comprising a high-dielectric electrically insulating layer disposed over the at least one sensor element.

6. The fetal heart monitoring system according to claim 1 wherein the backing plate is generally circular and has a perimetrical edge.

7. A fetal heart monitoring system comprising:
   a backing plate having a front surface and a back surface;
   at least one sensor element for acquiring acoustic fetal heart signals produced by a fetus within a body;
   the at least one sensor element being attached to the backing plate solely on the front surface;
   the front surface being configured to be disposed to face toward the body when the attached at least one sensor element is positioned for acquiring the fetal heart signals;

the front surface of the backing plate having a generally concave shape; and the back surface having a generally convex back surface.

8. A fetal heart monitoring system comprising:
a backing plate having a front surface and a back surface;
at least one sensor element for acquiring acoustic fetal heart signals produced by a fetus within a body;
the at least one sensor element being attached to the backing plate solely on the front surface;
a web belt; and
a web belt guide movably attached to the web belt, the web belt guide being attached to the back surface of the backing plate.

9. A fetal heart monitoring system, comprising:
a backing plate having a front surface and a back surface, wherein the backing plate is generally circular and has a perimetrical edge;
at least one sensor element attached to the front surface for acquiring acoustic fetal heart signals produced by a fetus within a body;
a web belt;
a web belt guide movably attached to the web belt;
a spacer block attached to the web belt guide and the back surface of the backing plate;
a plurality of wires, each of which receiving electrical signals from the at least one sensor element; and
a clamp attached to the web belt guide for harnessing the wires.

10. The fetal heart monitoring system according to claim 9 comprising an annular support member molded about the perimetrical edge of the backing plate, the spacer block and the clamp, the annular support member being fabricated from an electrically non-conductive material.

11. A fetal heart monitoring system, comprising:
a backing plate having a generally concave front surface and a generally convex back surface;
at least one sensor element attached to the concave front surface for acquiring acoustic fetal heart signals produced by a fetus within a body; and
the concave front surface being configured to be disposed to face toward the body when the attached at least one sensor element is positioned for acquiring the fetal heart signals.

12. The fetal heart monitoring system according to claim 1 wherein the at least one sensor element has a shape that conforms to the generally concave front surface of die backing plate.

13. The fetal heart monitoring system according to claim 1 wherein the at least one sensor element comprises:
an inner sensor element; and
a plurality of outer sensor elements surrounding the inner sensor element.

14. The fetal heart monitoring system according to claim 13 wherein the inner sensor element has a generally hexagonal shape and each of the outer sensor elements has a generally trapezoidal shape.

15. The fetal bean monitoring system according to claim 1 further comprising a high-dielectric electrically insulating layer disposed over the at least one sensor element.

16. The fetal heart monitoring system according to claim 1 wherein the backing plate is generally circular and has a perimetrical edge.

17. A fetal heart monitoring system comprising:
a backing plate having a generally concave front surface and a generally convex back surface;
at least one sensor element attached to the concave front surface for acquiring acoustic fetal heart signals produced by a fetus within a body;
a web belt; and
a web belt guide movably attached to the web belt, the web belt guide being attached to the convex back surface of the backing plate.

18. A fetal heart monitoring system, comprising:
a backing plate having a generally concave front surface and a generally convex back surface, wherein the backing plate is generally circular and has a perimetrical edge;
at least one sensor element attached to the concave front surface for acquiring acoustic fetal heart signals produced by a fetus within a body;
a web belt;
a web belt guide movably attached to the web belt;
a spacer block attached to the web belt guide and the back surface of the backing plate;
a plurality of wires, each of which receiving electrical signals from the sensor element; and
a clamp attached to the web belt guide for harnessing the wires.

19. The fetal heart monitoring system according to claim 18 comprising an annular support member molded about the perimetrical edge of the backing plate, the spacer block and the clamp, the annular support member being fabricated from an electrically non-conductive material.

20. A fetal heart monitoring comprising:
a backing plate having a generally concave front surface and a generally convex back surface; and
at least one sensor element attached to the concave front surface for acquiring acoustic fetal heart signals produced by a fetus within a body; and
wherein each sensor element comprises:
a first conductor;
a first electrically conductive adhesive layer disposed over a portion of the first conductor;
a first piezoelectric film layer disposed over the first electrically conductive adhesive layer;
a second conductor having a potion thereof disposed over the first piezoelectric layer;
a second electrically conductive adhesive layer disposed over said portion of the second conductor;
a second piezoelectric film layer disposed over the second electrically conductive adhesive layer;
a third conductor having a portion thereof disposed over the second piezoelectric film layer;
a third electrically conductive adhesive layer disposed over said portion of the third conductor; and
a metallic shield disposed over substantially the entire first and second piezoelectric films.

21. The fetal heart monitoring system according to claim 20 further comprising a jumper tab disposed over the third electrically conductive adhesive layer.

22. A fetal heart monitoring system comprising:
a backing plate having a front surface and a back surface;
at least one sensor element for acquiring acoustic fetal heart signals produced by a fetus within a body;
the at least one sensor element being attached to the backing plate solely on the front surface; and
wherein each sensor element comprises:
a first conductor;
a first electrically conductive adhesive layer disposed over a portion of the first conductor;

a first piezoelectric film layer disposed over the first electrically conductive adhesive layer;

a second conductor having a portion thereof disposed over the first piezoelectric layer;

a second electrically conductive adhesive layer disposed over said portion of the second conductor;

a second piezoelectric film layer disposed over the second electrically conductive adhesive layer;

a third conductor having a portion thereof disposed over the second piezoelectric film layer;

a third electrically conductive adhesive layer disposed over said portion of the third conductor; and a metallic shield disposed over substantially the entire first and second piezoelectric films.

23. The fetal heart monitoring system according to claim 22 further comprising a jumper tab disposed over the third electrically conductive adhesive layer.

* * * * *